United States Patent [19]

Vernon

[11] Patent Number: 4,596,562
[45] Date of Patent: Jun. 24, 1986

[54] SAFETY DEVICE AND METHOD FOR HANDLING SYRINGE NEEDLE COVERS

[76] Inventor: Jonathan T. Vernon, 215 E. Lantana Rd., Lantana, Fla. 33462

[21] Appl. No.: 701,966

[22] Filed: Feb. 14, 1985

[51] Int. Cl.⁴ ............................................. A61M 5/32
[52] U.S. Cl. .................................... 604/192; 604/263
[58] Field of Search ............................... 604/192, 263

[56] References Cited
PUBLICATIONS
Comp Gard TM Comp Equipment Corp. Brochure.

Primary Examiner—John D. Yasko
Attorney, Agent, or Firm—Victor F. Volk

[57] ABSTRACT

A hand tool for holding a syringe needle cover prevents accidental pricking when it is replaced, and comprises a slot between parallel plates, into which the needle cover flange can be wedged. Tapered needle covers are gripped by holes in the tool, providing a safe method for handling syringes.

10 Claims, 5 Drawing Figures

U.S. Patent   Jun. 24, 1986   4,596,562
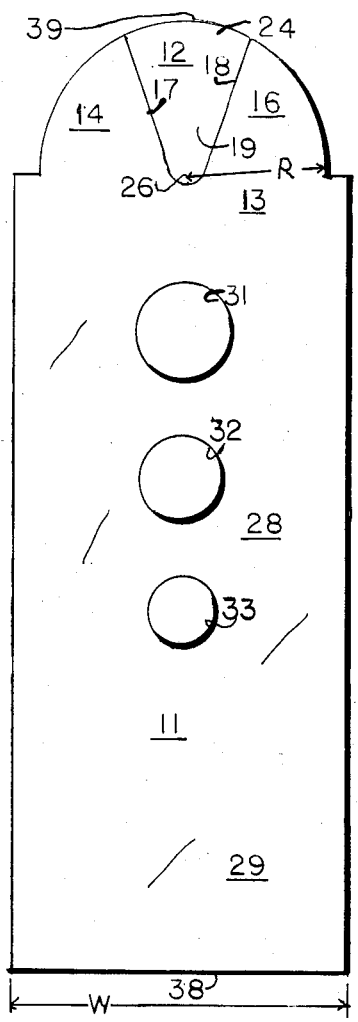
FIG. 1
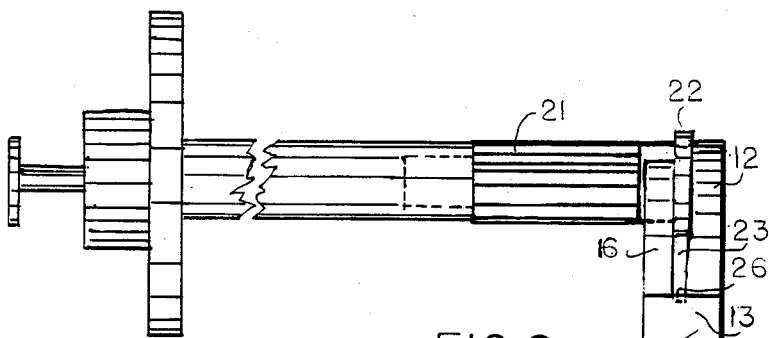
FIG. 2
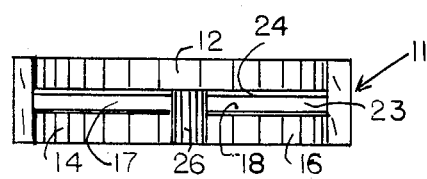
FIG. 3
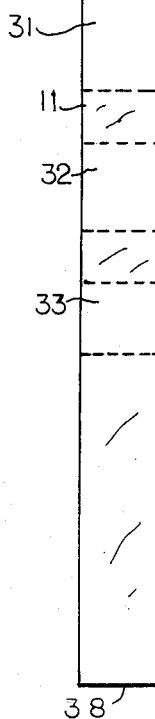
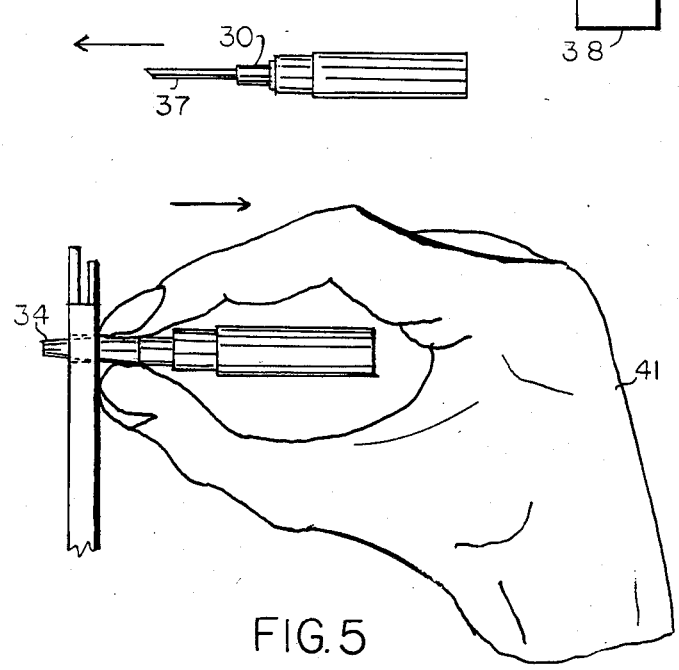
FIG. 4   FIG. 5

SAFETY DEVICE AND METHOD FOR HANDLING SYRINGE NEEDLE COVERS

BACKGROUND OF THE INVENTION

Accidental pricking is a serious problem for persons who must handle hypodermic needles. The pricking is most apt to occur to the fingers that hold a needle cover, in the act of replacing the cover, and almost all covers must be replaced, even for disposable needles for it is hazardous to throw a used syringe into the trash with an exposed needle. Needles with plastic needle covers are used in large quantities and in standard sizes and shapes. Widely used disposable insulin needles have covers of ridge lined cylindrical shape, with flanged tops, while most, including luer lock, other needles have tapered covers, varying in length to fit different length needles but being provided in a short range of diameters.

When the needles are re-covered it is usually after they have been removed from a patient and are contaminated with the patient's microorganisms, such, possibly, as AIDS virus. It is thus a matter of grave concern to nurses and hospital assistants that they be protected from the danger of pricking their fingers when they replace a needle cover. The covers, however, present a very small target when held in one's hand, and if this target is missed by the syringe needle, a dangerous skin breaking by the contaminated needle is almost inevitable. In practical terms there has been no solution to this problem prior to the present invention.

SUMMARY OF THE INVENTION

I have invented a safety device for grippingly supporting a flanged syringe needle cover, comprising a base with a back platelike member extending from it. Two other coplanar platelike members extend from the base, generally parallel to the back platelike member. These are spaced from the back member enough so that a flat wall of the back member and opposing flat walls of the other two members define a slot for receiving the flange of the cover, and the edges of the other two members define a channel, at least a portion of which is narrower than the flange but wide enough for the reception of the cover. Handle means extend from the base oppositely to the platelike members so that the cover can be firmly held but any human fingers are remote from the line of insertion of a needle into the cover. In some embodiments either the slot or the channel or both may be tapered toward the base, and in a preferred embodiment the platelike members and the base are homogeneously integral with the handle. My device may advantageously comprise a plate comprising walls defining at least one aperture that is dimensioned to grippingly support a tapered syringe needle cover.

Using my device I have originated a method for routinely replacing tapered syringe needle covers without danger of pricking the hand that holds the cover. In this method I follow the steps of inserting the cover into a hole through both surfaces of a plate, the hole being dimensioned to grippingly support the cover, holding the plate with one hand at a location remote from the hole bearing the cover, bringing the plate and needle together so that the needle enters and fits snugly into the cover, and then grasping the cover in one hand and the plate in the other, withdrawing the cover, including the needle, from the plate.

I have also originated another method, for routinely replacing flanged syringe needle covers, without danger of pricking the hand that holds the cover. In this method I follow the steps of inserting the cover flange into a slot between platelike members extending from a base that is attached to a handle means, holding the handle means with one hand at a location remote from the slot, and bringing together the platelike members and the needle so that the needle enters and fits snugly into the cover. Then while grasping the cover in one hand and the handle means in the other, I withdraw the flange, with the cover including the needle, from the slot.

BRIEF DESCRIPTION OF THE DRAWINGS

FIG. 1 shows an enlarged front view of a device of my invention.

FIG. 2 shows an end view of the device of FIG. 1 holding an insulin syringe by its flanged cover.

FIG. 3 shows an enlarged end view of the device of FIGS. 1 and 2.

FIGS. 4 and 5 show a method of using the device of my invention.

DETAILED DESCRIPTION OF PREFERRED EMBODIMENTS

Referring to FIG. 1, which shows a preferred one of my devices 11 about double size, a back platelike member 12 extends from a base 13 from which also extend coplanar platelike members 14 and 16 whose respective edges 17, 18 comprise a channel 19 that is wide enough to receive a needle cover 21 but narrow enough to engage a flange 22 of the cover 21 when the latter is pressed into a slot 23 created by opposing flat walls 24, 26 of the respective platelike platelike members 16, 14 and 12. The channel 19 tapers toward the base 13 so that, while an upper opening 24 of the channel is wider than the diameter of the cover 21, a bottom 26 of the channel 19 is narrower than the cover. Thus the cover will be wedged into the channel if it is forced down far enough. In the preferred illustrated example the opening of the channel is 0.375 in. (9.53 mm), tapering down to 0.219 in. (5.56 mm). However, wedging of the cover 21 into the tapered channel 19 does not necessarily occur because the slot 23 is also tapered toward the base 13, from a top slot width, in the present example, of 0.047 in. (1.2 mm) to a width at the bottom of the slot of 0.034 in. (0.86 mm) and, surprisingly, the flange 22 wedges in the slot 23 firmly enough to support not only the cover 21 but also an attached syringe 27, before the walls of the cover 21 engage the edges 17, 18.

The cover can safely be inserted into the device 11 by finger pressure against the top of the flange 22. However, the circular outline of the top portion of the device facilitates "rolling" it over the cover of a syringe that is lying on any rigid flat surface, and thus engaging the cover flange in the slot 23 without manually holding the syringe at all.

The base 13 might, within the scope of my invention, be secured to a cylindrical handle, not shown, but I prefer that the base 13 comprise the top portion of an integral slab or block which comprises a plate portion 28 and a handle portion 29. Three holes 31, 32, 33, having respective diameters of 5/16, 9/32, and ¼ inches (7.9, 7.1, and 6.35 mm) are machined through the plate portion 28 since I have found that at least one of these holes in the plate portion 28 will grippingly support any of the commonly used tapered needle covers, such as a cover 34 (FIG. 4) and provide a safe method for re-covering the needle. This is due to the fact that human fingers 36, holding my device by its handle 29 are remote from the line of motion of a needle 37 being inserted into the cover, where it will fit snugly due to a conventional needle hub 30 engaging a conventional cylindrical portion 35 of the cover.

My device my advantageously be made of synthetic polymeric material such as, but not limited to methyl methacrylate, nylon, and polycarbonate. It may also be made of stainless steel or glass, but synthetic polymer has an advantage of economy. The material used should be capable of polishing to a smooth, washable surface, and should be stable at sterilization temperatures. Although I have tapered the slot 23 and channel 19, I have found that, if the slot is not tapered but has a width somewhat smaller than that of the flange, it will assume a tapered contour when a flange is forced into it. And, if the flange is gripped sufficiently by the slot, the edges 17,18 may be parallel, forming a straight channel so long as its width exceeds that of the cover 21 and is sufficiently less than that of the flange 22.

Referring again to FIGS. 4 and 5, after the needle has been safely inserted into the cover the cover is removed from the plate portion 28 by grasping it in the other hand 41. A similar method is applied to flanged needle covers. Here the cover is held by its flange in the slot 23, the fingers 36 being, in this case, also remote from the line of motion of the needle.

A preferred example of my invention, comprising homogeneous synthetic polymer has an overall length between a bottom 38 of the handle 29 and a top 39 of the platelike member 12, of 3⅛ in. (8.25 cm), a width W of the device 11 of 1⅛ in. (2.9 cm), and a thickness T (FIG. 2) of 0.25 in. (6.35 mm).

The foregoing description has been exemplary rather than definitive of my invention for which I desire an award of Letters Patent as defined in the appended claims.

I claim:

1. A device for grippingly supporting a flanged needle cover comprising:
   A. a base,
   B. A back platelike member comprising at least one flat wall extending from said base,
   C. two coplanar platelike members, each comprising at least one flat wall, extending from said base generally parallel to said back member, said two members being spaced from said back member said flat wall of said back member and said flat walls of said two members defining a slot gripping the flange of said cover,
   D. said two members comprising edges defining a channel portion narrower than said flange for the reception of said cover, and
   E. handle means extending from said base oppositely to said platelike members, whereby said cover can be held with human fingers that are remote from the line of insertion of a needle therein.

2. The device of claim 1 wherein said slot is tapered toward said base.

3. The device of claim 1 wherein said channel is tapered toward said base.

4. The device of claim 1 wherein said base and said platelike members are homogeneously integral with said handle.

5. The device of claim 4 comprising a synthetic polymeric material of construction.

6. The device of claim 1 wherein said flat wall of said back platelike member is spaced about 0.04 in. (1 mm) from said flat walls of said two platelike members and said channel comprises an opening of about 0.28 in. (7 mm).

7. The device of claim 1 comprising a plate comprising walls defining at least one aperture therethrough, said aperture being dimensioned to grippingly support a tapered syringe needle cover.

8. The device of claim 7 comprising three of said apertures, said aperatures being circular with diameters of about 5/16, 9/32, and ¼ inches (7.9, 7.1 and 6.35 mm).

9. The method of safely replacing a tapered syringe needle cover comprising the steps of:
   A. inserting said cover into an aperture through both faces of a plate of the device of claim 1, said hole being dimensioned to grippingly support said cover,
   B. holding said plate with one hand at a location remote from said aperture,
   C. bringing together said plate and said needle so that said needle enters and fits snugly into said cover, and
   D. While grasping said cover in one hand and said plate in the other, withdrawing said cover, inclosing said needle, from said plate.

10. The method of safely replacing a flanged syringe needle cover, comprising the steps of:
   A. inserting the flange of said cover into a slot between a back member and two spaced coplanar platelike members extending from a base that is attached to handle means,
   B. holding said handle means with one hand at a location remote from said slot,
   C. bringing together said platelike members and said needle so that said needle enters and fits snugly into said cover, and
   D. while grasping said cover in one hand and said handle means in the other, withdrawing said flange, said cover including said needle, from said slot.

* * * * *